(12) United States Patent
Harnsberry et al.

(10) Patent No.: US 12,281,257 B2
(45) Date of Patent: Apr. 22, 2025

(54) SOLIDS REMOVAL USING SOLVENT BLENDS COMPRISING A DISULFIDE SOLVENT

(71) Applicant: EXXONMOBIL UPSTREAM RESEARCH COMPANY, Spring, TX (US)

(72) Inventors: Kevin A. Harnsberry, Beaumont, TX (US); P. Scott Northrop, Spring, TX (US)

(73) Assignee: EXXONMOBIL UPSTREAM RESEARCH COMPANY, Spring, TX (US)

( * ) Notice: Subject to any disclaimer, the term of this patent is extended or adjusted under 35 U.S.C. 154(b) by 38 days.

(21) Appl. No.: 18/256,359

(22) PCT Filed: Oct. 11, 2021

(86) PCT No.: PCT/US2021/071808
§ 371 (c)(1),
(2) Date: Jun. 7, 2023

(87) PCT Pub. No.: WO2022/126044
PCT Pub. Date: Jun. 16, 2022

(65) Prior Publication Data
US 2024/0018410 A1   Jan. 18, 2024

Related U.S. Application Data

(60) Provisional application No. 63/123,015, filed on Dec. 9, 2020.

(51) Int. Cl.
  C09K 8/532 (2006.01)
  C07C 7/10 (2006.01)
  C09K 8/524 (2006.01)

(52) U.S. Cl.
  CPC ............ *C09K 8/532* (2013.01); *C07C 7/10* (2013.01); *C09K 8/524* (2013.01)

(58) Field of Classification Search
None
See application file for complete search history.

(56) References Cited

U.S. PATENT DOCUMENTS

| | | | |
|---|---|---|---|
| 3,700,594 A | 10/1972 | Lissant | |
| 3,846,311 A * | 11/1974 | Sharp | C09K 8/532 299/5 |
| 4,217,955 A * | 8/1980 | Sigmund | E21B 43/164 166/402 |
| 5,104,557 A * | 4/1992 | Lindstrom | C09K 8/532 507/90 |
| 7,708,864 B2 * | 5/2010 | Brons | G01N 33/28 436/805 |
| 2020/0002599 A1 * | 1/2020 | Northrop | C09K 8/532 |

FOREIGN PATENT DOCUMENTS

WO   2020005524 A1   1/2020

* cited by examiner

*Primary Examiner* — John J Figueroa
(74) *Attorney, Agent, or Firm* — Vorys, Sater, Seymour and Pease LLP

(57) ABSTRACT

Solids dissolution may be promoted using a solvent blend comprising a disulfide solvent, particularly additional solids present in combination with elemental sulfur deposits. The solvent blends may comprise at least one disulfide solvent, at least one amine solvent, at least one ketone solvent, at least one ester solvent, and optionally water. Solids dissolution methods may comprise: identifying one or more solids in addition to elemental sulfur to be contacted by the solvent blend; adjusting a composition of the solvent blend to afford selectivity for dissolution of at least a portion of the one or more solids; and contacting the solvent blend with elemental sulfur and the one or more solids to promote at least partial dissolution thereof.

14 Claims, No Drawings

SOLIDS REMOVAL USING SOLVENT BLENDS COMPRISING A DISULFIDE SOLVENT

This application claims the priority benefit of U.S. Provisional Patent Application No. 63/123,015 filed Dec. 9, 2020, entitled SOLIDS REMOVAL USING SOLVENT BLENDS COMPRISING A DISULFIDE SOLVENT.

FIELD

The present disclosure relates to dissolution of solids with disulfide solvents.

BACKGROUND

Solids (e.g., metal-containing compounds, asphaltenes, paraffins, elemental sulfur, and the like) may become deposited in conjunction with various activities associated with production of a hydrocarbon resource from a subterranean formation. Elemental sulfur deposition may be particularly prevalent in sour gas reservoirs and in subterranean formations containing sulfur-containing organic compounds. When additional solids are present in combination with elemental sulfur, removal of the combined elemental sulfur and additional solids may be exceedingly problematic. Excessive solids deposition of various types may impede production, or in even more serious scenarios, plug lines, tubing, valves or other equipment, thereby rendering a well facility inoperable.

Solids deposition represents one of the major flow assurance issues in oil production processes. Mechanical removal of deposited solids has been a widely used technique, such as for removing paraffinic wax deposits, but such procedures may be rather costly and time consuming. Heating is another technique frequently used for promoting removal of solids, but doing so can cause formation damage if applied downhole. Bacterial treatments to promote biodegradation of solids is another commonly used technique, but only specific site conditions may be tolerated and the range of solids removable is rather small. Solvent-based techniques for removal of solids remain one of the preferred choices. Unfortunately, it is all too common to encounter multiple types of solids in an oilfield assembly also containing elemental sulfur deposits. When additional solids are present in combination with elemental sulfur, it can be exceedingly problematic to remove both the elemental sulfur and the additional solids. The elemental sulfur may prevent the solvent from effectively contacting a co-precipitated solid. Conversely, a co-precipitated solid may prevent elemental sulfur from being dissolved by a solvent suitable for dissolving elemental sulfur. Using sequential washes having different dissolution properties to remove elemental sulfur and other deposits may be problematic, costly, and time consuming.

Although some solvents are capable of dissolving large quantities of elemental sulfur, there are various challenges associated with their use. Carbon disulfide, for instance, is highly volatile, odorous, and extremely flammable. Disulfides present several advantages when used as solvents for dissolving elemental sulfur, but their excessive odor may likewise present significant operational difficulties. In fact, the extreme odor of disulfide solvents may require such extensive engineering controls to preclude discharge of even minute solvent quantities that it may become essentially impractical to use them effectively. In addition, disulfide solvents alone may be rather ineffective for dissolving other types of solids that may be present in combination with elemental sulfur deposits.

Diaryl disulfide (DADS) is one example of a disulfide solvent having sufficiently low odor to facilitate its practical use. Unfortunately, commercial production of this chemical has been curtailed, and it is becoming scarce in bulk quantities. Dimethyl disulfide is an effective solvent for dissolving elemental sulfur, and would be a suitable replacement for diaryl disulfide, except for the operational challenges associated with its extreme odor.

U.S. Patent Application Publication 20200002599 describes solvent mixtures containing dimethyl disulfide that have significantly reduced odor. In particular, in addition to dimethyl disulfide, the solvent mixtures having a reduced odor profile contain an odorant fraction comprising an amine, a ketone, and ethyl lactate. Without being bound by theory or mechanism, the odorant fraction is believed to suppress olfactory receptors by providing competing strong smells and decrease the perceived odor associated with dimethyl disulfide.

SUMMARY

In some embodiments, the present disclosure provides methods for promoting solids dissolution using a solvent blend comprising a disulfide solvent, particularly additional solids present in combination with one or more sulfur deposits. The methods comprise: providing a solvent blend comprising at least one disulfide solvent, at least one amine solvent, at least one ketone solvent, and at least one ester solvent; identifying one or more solids in addition to elemental sulfur to be contacted by the solvent blend; adjusting a composition of the solvent blend to afford selectivity for dissolution of at least a portion of the one or more solids; and contacting the solvent blend with elemental sulfur and the one or more solids to promote at least partial dissolution thereof.

In some embodiments, the present disclosure provides methods for promoting inorganic solids dissolution using a solvent blend comprising a disulfide solvent, particularly additional inorganic solids present in combination with one or more sulfur deposits. The methods comprise: providing a solvent blend comprising at least one disulfide solvent, at least one amine solvent, at least one ketone solvent, and at least one ester solvent; exposing the solvent blend to conditions such that at least a portion of the at least one ester solvent hydrolyzes to at least one carboxylic acid, thereby affording an at least partially spent solvent blend; and contacting the at least partially spent solvent blend with an inorganic sulfide to promote dissolution of a least a portion thereof.

BRIEF DESCRIPTION OF THE DRAWINGS

Not applicable.

DETAILED DESCRIPTION

The present disclosure relates to solids dissolution using a disulfide solvent and, more particularly, methods for promoting solids dissolution using a solvent blend comprising a disulfide solvent, particularly additional solids present in combination with one or more sulfur deposits.

As discussed above, disulfide solvents may be particularly effective for dissolving sulfur deposits, such as in sour gas wells and in wellbore equipment associated therewith.

Excessive odor of disulfide solvents, such as dimethyl disulfide, may make their use exceedingly problematic. Excessive odor of disulfide solvents may be mitigated by combining additional co-solvents that convey a suitable overall odor profile to the resulting solvent blend, while not substantially impacting the sulfur dissolution capabilities relative to the disulfide solvent alone, and in some instances even enhancing the dissolution capabilities. In the disclosure herein, the solvent blend may be referred to as being "odor balanced" or a grammatical form thereof, when one or more disulfide solvents and additional co-solvents are present at a ratio sufficient to maintain a suitable overall odor profile. Competing strong smells are believed to render the odor of the solvent blend overall less objectionable to olfactory receptors.

Other solids may frequently be deposited in an oilfield assembly in combination with elemental sulfur. Other solids that may be present in an oilfield assembly alone or in combination with elemental sulfur may include, for example, inorganic solids such as metal sulfides and organic solid materials such as polyaromatic compounds, diamondoid compounds, paraffinic compounds, and any combination thereof. Surprisingly, these solids may undergo dissolution with odor-balanced solvent blends also effective for promoting dissolution of elemental sulfur. Even more surprisingly, the composition of the solvent blends may be tailored to promote dissolution of particular solids, usually without substantially impacting the dissolution of elemental sulfur. Additional details on how the solvent blends may be tailored to promote preferential dissolution of one type of solid over another follows hereinbelow.

All numerical values within the detailed description and the claims herein are modified by "about" or "approximately" with respect to the indicated value, and take into account experimental error and variations that would be expected by a person having ordinary skill in the art. Unless otherwise indicated, ambient temperature (room temperature) is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A," and "B."

For the purposes of the present disclosure, the new numbering scheme for groups of the Periodic Table is used. In said numbering scheme, the groups (columns) are numbered sequentially from left to right from 1 through 18.

The terms "solids," "solid deposits" and "deposits" may be used interchangeably.

As used herein, the term "disulfide solvent" refers to any organic compound containing a sulfur-sulfur bond (i.e., R—S—S—R, wherein R is a hydrocarbyl group).

As used herein, the term "elemental sulfur" refers to any zero-valent polymorph of sulfur.

As used herein, the term "aromatic" or "aromatic hydrocarbon" refer to a hydrocarbon or hydrocarbyl group having a cyclic arrangement of conjugated pi-electrons that satisfies the Hückel rule. The term "polyaromatic" refers to an organic compound containing at least two aromatic rings, preferably fused aromatic rings.

The present disclosure provides methods in which a solvent blend comprising at least one disulfide solvent, at least one amine solvent, at least one ketone solvent, and at least one ester solvent may be utilized to promote dissolution of solids in addition to elemental sulfur, preferably by tailoring the composition of the solvent blends depending on the type of solids that are present in a given location. Tailoring of the solvent blends may be performed during formulation of the solvent blends or "on-the-fly" after identifying particular solids that are present in a given location.

Such methods of the present disclosure may comprise: providing a solvent blend comprising at least one disulfide solvent, at least one amine solvent, at least one ketone solvent, and at least one ester solvent; identifying one or more solids in addition to elemental sulfur to be contacted by the solvent blend; adjusting a composition of the solvent blend to afford selectivity for dissolution of at least a portion of the one or more solids; and contacting the solvent blend with elemental sulfur and the one or more solids to promote at least partial dissolution thereof. Additional details directed to solvent blends suitable for use in the present disclosure follow hereinbelow. As used herein, the term "selectivity" and grammatical forms thereof refers to the preference for dissolving a particular solid over another. A solvent blend of the present disclosure may be "selective" relative to an unmodified solvent blend containing specified base amounts of at least one disulfide solvent, at least one amine solvent, at least one ketone solvent, at least one ester solvent, and optionally a specified amount of water. That is, a solvent blend whose composition has been adjusted to provide selectivity for dissolving a particular solid may at least partially dissolve a greater amount of that solid compared to a different solid that the solvent blend could potentially dissolve. Preferably, even after modification, the solvent blends may maintain a high capacity for dissolving elemental sulfur and/or one or more solids.

According to some embodiments of the present disclosure, a base solvent blend may be modified to afford selectivity for a given solid by regulating an amount of water present in the solvent blends. Up to about 20 wt. % water may be present to afford a particular degree of selectivity. Without being bound by theory or mechanism, the selectivity toward dissolution of a particular solid may result from changing the polarity of the solvent blends at specified amounts of water. In addition, the Hildebrand solubility parameter of the solvent blend may be adjusted (e.g., through addition of water or a particular co-solvent) to approach the Hildebrand solubility parameter of a given solid. Temperature and pressure may also impact the solubility of a given solid. For example, under supercritical conditions, dissolution of a particular solid may become favored in preference to a different solid. In at least one embodiment of the present disclosure, selectivity of a solvent blend toward a given solid may be determined at a temperature of about 150° F. or greater, and at about 20 wt. % water or less, as measured relative to the solvent blend as a whole.

Contacting the one or more solids with the solvent blend to promote dissolution thereof may occur under heating conditions, such as at a temperature of about 100° F. or above, or about 150° F. or above, or about 200° F. or above, or about 250° F. or above in non-limiting embodiments. In some instances, heating may be performed under a pressure suitable to maintain the solvent in a liquid phase, including under supercritical conditions. In addition, contacting may occur under static or dynamic (flowing) conditions with respect to the solvent blend.

Advantageously, the water content of the solvent blends and adjustment of the amount thereof may provide a flexible way for adjusting the composition of the solvent blends to afford dissolution of a given solid. Reactions promoted by water may also afford an additional degree of selectivity. More specifically, under suitable conditions, water in the solvent blends may promote ester hydrolysis, which may lead to formation of a chelant species for promoting dissolution of particular solids, specifically a chelant species derived from the at least one ester solvent, such as lactic acid derived from ethyl lactate. In addition, the water content of the solvent blends may surprisingly be adjusted to promote dissolution of asphaltenes in preference to paraffinic compounds (e.g., waxes), which is surprising given the dissimilarity of water and the non-polar polyaromatic character of asphaltenes. Beyond a threshold amount of water, the solubility of asphaltenes may become much less. For dissolving asphaltenes and elemental sulfur, the water content of the solvent blends may be up to about 25 wt. %, based on the total volume of the solvent blend.

In other instances, the solvent blends may have their compositions adjusted through direct addition of further quantities of the one or more disulfide solvents, the one or more ketone solvents, the one or more amine solvents, and/or the one or more ester solvents. Suitable quantities of water may likewise be introduced to the solvent blends to promote dissolution of a particular solid, as referenced above. Added solvents may be introduced in a proportion to maintain odor balance, while also promoting solids dissolution, as a non-limiting example.

The one or more solids that may undergo dissolution according to the disclosure herein may comprise an organic solid material such as polyaromatic compounds, diamondoid compounds, paraffinic compounds, and any combination thereof. Under suitable conditions, polyaromatic compounds, such as asphaltenes, may be dissolved in preference to diamondoid compounds and paraffinic compounds, optionally in combination with dissolution of elemental sulfur.

Polyaromatic compounds that may undergo dissolution according to the disclosure herein may comprise an organic material selected from the group consisting of dibenzothiophenes, asphaltenes, pyrenes, chrysenes, naphthalenes, anthracenes, and any combination thereof.

Diamondoid compounds that may undergo dissolution according to the disclosure herein may comprise an organic material selected from the group consisting of adamantane, diamantane, triamantane, tetramantane, pentamantane, cyclohexamantane, super-adamantane, any isomers thereof, and any combination thereof.

Paraffinic compounds that may undergo dissolution according to the disclosure herein may comprise at least one $C_{15}$-$C_{30}$ paraffinic wax, including branched or unbranched waxes within this size range. At suitable compositions of the solvent blend, asphaltenes may be dissolved preferentially over paraffinic compounds, as described above.

Inorganic solids such as inorganic sulfides may undergo dissolution with the solvent blends as well, sometimes after the solvent blends become at least partially spent through ester hydrolysis, as referenced in brief above and described hereinafter. In some examples, the one or more solids undergoing dissolution according to the disclosure herein may comprise at least one solid selected from the group consisting of iron sulfides, arsenic sulfides, dibenzothiophene, asphaltenes, waxes, and any combination thereof, particularly wherein at least one inorganic solid is present, more particularly an inorganic sulfide.

Ester hydrolysis may generate an acid and an alcohol, as well as consume water from a solvent blend, thereby changing the solvent blend's compositional makeup. Surprisingly, the alcohols and carboxylic acids generated during this process do not appreciably impact the solubility of elemental sulfur in the solvent blends, even when significant quantities of water remain. Acid generation may be desirable in many instances, such as to dissolve a portion of the subterranean matrix in a carbonate formation to which the solvent blend is introduced. Dissolution of a portion of the subterranean matrix may stimulate increased production of a hydrocarbon resource. Moreover, carboxylic acids generated through ester hydrolysis, particularly dicarboxylic acids generated from esters such as lactate esters or glycolic acid esters, may promote at least partial dissolution of metal-containing solids (inorganic solids), when present. More specifically, metal-containing solids (e.g., compounds containing transition metal ions or main group metal ions, such as iron or arsenic) may undergo chelation as carboxylic acids are produced through ester hydrolysis. Further, as water is consumed, an initially biphasic mixture form of the solvent blends disclosed herein may be converted to an emulsion or similar homogeneous mixture. Without being bound by theory or mechanism, the chelating ability may be influenced by the presence of the hydroxyl ions during the hydrolysis reaction between water and ethyl lactate or a similar ester to produce lactic acid and ethanol. Lactate ions may promote metals dissolution through chelation. Metal-containing solids can remain dissolved in solution after reacting with the solvent blends through chelation in the manner specified above. As the water content of the solvent blends changes, dissolution properties for other co-precipitated solids may also change, as specified above.

Accordingly, some methods of the present disclosure may comprise: providing a solvent blend comprising at least one disulfide solvent, at least one amine solvent, at least one ketone solvent, and at least one ester solvent; exposing the solvent blend to conditions such that at least a portion of the at least one ester solvent hydrolyzes to at least one carboxylic acid, thereby forming an at least partially spent solvent blend; and contacting the at least partially spent solvent blend with an inorganic solid, particularly an inorganic sulfide, to promote dissolution of a least a portion thereof. Other types of inorganic solids containing metal ions may undergo dissolution under similar conditions as well. Contact of the at least partially spent solvent blend with the inorganic sulfide or similar inorganic solid may occur under heating conditions, such as at a temperature of about 100° F. or above, or about 150° F. or above, or about 200° F. or above, or about 250° F. or above in non-limiting embodiments, optionally under a pressure above atmospheric pressure, including under supercritical conditions. Such conditions may also be conducive to promoting ester hydrolysis.

The at least one inorganic sulfide may comprise a transition metal sulfide, a Group 15 sulfide, a main group sulfide, or any combination thereof. In more particular embodiments, the at least one inorganic sulfide may comprise arsenic sulfide, iron sulfide, copper sulfide, magnesium sulfide, or any combination thereof. Without being bound by any theory or mechanism, some methods of the present disclosure may include polysulfide ($S_x^{2-}$) formation as at least a portion of the dissolution mechanism. Advantageously, metal ions in such compounds can have solubility in water following contact with weak organic acids, such as lactic acid, formed through hydrolysis of the at least one ester (e.g., ethyl lactate). Solubility of chelated metal ions and other byproducts may increase with temperature. For instance, the solubility of metal lactates may increase from about 0.1 mg/L at 50° F. to at least about 5 mg/L at 200° F., or from about 1 mg/L at 50° F. to at least about 5 mg/L at 200° F., or from about 1.5 mg/L at 50° F. to at least about 5 mg/L at 200° F. Solubility values of about 6 mg/L, about 7 mg/L, about 8 mg/L, about 10 mg/L, about 15 mg/L, about 20 mg/L or even higher at 200° F. may be possible through application of the disclosure herein.

Solvent blends suitable for dissolving solids in addition to elemental sulfur according to the present disclosure may comprise at least one disulfide solvent, and multiple co-solvents comprising at least one amine solvent, at least one ketone solvent, and at least one ester solvent. As referenced above, the co-solvents, when suitably chosen and present in a sufficient ratio with respect to each other and with respect to the at least one disulfide solvent, may suppress odor and promote dissolution of solids and/or chelation of metal ions from solids. Further disclosure follows below regarding these co-solvents and suitable amounts thereof for promoting odor suppression and at least partial dissolution of solids.

[The solvent blends utilized herein may exhibit decreased odor intensity or offensiveness and/or decreased perceived intensity or offensiveness, as evaluated relative to the intensity or offensiveness of the disulfide solvent alone, perceived or otherwise. As a non-limiting example, the solvent blends, when odor-balanced, may have a pleasant or more pleasant odor or perceived odor, and/or be less offensive/malodorous, as compared to the disulfide solvent alone. The co-solvents, in addition to conveying specific chemical and physical properties to the solvent blends, may impart contrasting and distinct odors to the solvent blends, thereby affording an acceptable odor balance (overall odor profile) to the solvent blends as a whole. Without being bound by theory or mechanism, the combination of the at least one disulfide solvent and the co-solvents may confuse and/or otherwise overwhelm the olfactory system organs of an individual who smells the solvent mixture, thereby causing an acceptable overall odor profile to be perceived by the individual. Such a phenomenon may be referred to herein as a "white smell effect" and/or "white smell odor."

The odor intensity and/or decrease in the odor intensity of the solvent blends, including spent or partially spent variants thereof may be measured and/or quantified in any suitable manner. As an example, the solvent blends may have a perceived intensity, relative to the odor of a disulfide solvent alone (i.e., a disulfide solvent contained in a given solvent blend), differing by at least about 1, by at least about 2, by at least about 3, by at least about 4, and/or by at least about 5 on an Odor Intensity Referencing Scale, as defined by ASTM E544-99. Such Odor Offensiveness Referencing Scales generally are subjective in nature and typically utilize panelists to rank odors on a scale of 0 to 10, with 0 indicating that the odor is not offensive/intense and 10 indicating that the odor is very offensive/intense.

The offensiveness and/or decrease of the offensiveness of the solvent blends, including spent or partially spent variants thereof may similarly be measured and/or quantified in any suitable manner. As an example, the solvent blends may have a perceived offensiveness, relative to the offensiveness of the odor of a given disulfide solvent alone, differing by at least about 1, by at least about 2, by at least about 3, by at least about 4, and/or by at least about 5 on an Odor Offensiveness Referencing Scale.

The solvent blends disclosed herein, including spent or partially spent variants thereof may further comprise dissolved elemental sulfur and/or one or more dissolved solids. The amount of elemental sulfur dissolved in the solvent blends may depend upon the quantity of elemental sulfur contacted with the solvent blends and the solubility limit of elemental sulfur in the solvent blends. As non-limiting examples, the solvent blends may feature a solubility limit for elemental sulfur of about 5 wt. % or above as measured relative to the solvent blend as a whole, or about 10 wt. % or above, or about 15 wt. % or above, or about 20 wt. % or above, or about 25 wt. % or above, or about 30 wt. % or above, or about 40 wt. % or above, or about 50 wt. % or above, or about 60 wt. % or above, or about 70 wt. % or above, or about 80 wt. % or above, or about 90 wt. % or above, or about 100 wt. % or above, or about 110 wt. % or above. The maximum solubility of elemental sulfur may be about 120 wt. %, but practical solubility values may be in a lower range due to viscosity issues and potential precipitation as the concentration nears the solubility limit. The foregoing solubility limits may be measured at standard temperature and pressure (1 atm and 25° C.). Preferably, the amount of dissolved elemental sulfur and other dissolved solids does not exceed the solubility limit in the solvent blends, either before or after becoming at least partially spent, to preclude unwanted deposition of sulfur and/or dissolved solids from the solvent blends in an undesired location.

In some instances, the solvent blends may have a maximum solubility of elemental sulfur that is less than that of the solubility in the at least one disulfide solvent alone. As examples, the maximum solubility of elemental sulfur may be about 10 wt. % or less, about 20 wt. % or less, about 30 wt. % or less, about 40 wt. % or less, about 50 wt. % or less, about 60 wt. % or less, about 70 wt. % or less, or about 80 wt. % or less of the maximum elemental sulfur solubility.

The solvent blends may comprise the one or more disulfide solvents in an amount of about 20 wt. % or greater, as measured relative to the solvent blend as a whole. More particular examples of the solvent blends may comprise about 30 wt. % or greater, or about 40 wt. % or greater of the at least one disulfide solvent, as measured relative to the solvent blend as a whole. Still more particular examples of the solvent blends may include those featuring about 20 wt. % to about 50 wt. % of the at least one disulfide solvent, or about 25 wt. % to about 45 wt. % of the at least one disulfide solvent, each as measured relative to the solvent blend as a whole. The foregoing amounts may be representative of the amount of the at least one disulfide solvent in as-prepared solvent blends, as well as in solvent blends that have become at least partially spent through loss or consumption of at least one co-solvent, such as through ester hydrolysis.

In particular embodiments, the at least one disulfide solvent may comprise or consist essentially of dimethyl disulfide (DMDS). The solvent blends may comprise at least about 20 wt. % DMDS, at least about 22 wt. % DMDS, at least about 24 wt. % DMDS, at least about 26 wt. % DMDS, at least about 28 wt. % DMDS, or at least about 30 wt. % DMDS in particular embodiments of the present disclosure. Additionally or alternatively, the solvent blends may comprise at most about 50 wt. % DMDS, at most about 45 wt. % DMDS, at most about 40 wt. % DMDS, at most about 35 wt. % DMDS, or at most about 30 wt. % DMDS.

In addition to at least one disulfide solvent in the amounts referenced above, the as-prepared solvent blends may comprise up to about 25 wt. % water, preferably up to about 20 wt. % water, as measured relative to the solvent blend as a whole. The amount of water present may be sufficient to partition the solvent blends into a biphasic mixture, or the amount of water may be low enough such that the solvent blends are emulsified or otherwise form a homogeneous mixture. Tailoring of the amount of water may dictate the preference of the solvent blends for dissolving asphaltenes over paraffins in a non-limiting example. The remaining balance of the solvent blends may collectively comprise the at least one amine solvent, the at least one ketone solvent, and the at least one ester solvent. Thus, in particular examples, the amount of the at least one amine solvent, the at least one ketone solvent, and the at least one ester solvent may collectively range from about 30 wt. % to about 80 wt. %, or about 40 wt. % to about 70 wt. % of the solvent blends. More specific disclosure regarding suitable examples of these solvents and particular amounts thereof to promote at least partial dissolution of one or more solids or elemental sulfur are provided hereinafter. The chosen co-solvents and the amounts thereof may be further selected to provide odor balance while accomplishing the foregoing.

The solvent blends may comprise up to about 25 wt. % of the at least one amine solvent, as measured relative to the solvent blend as a whole. Suitable amines may include, but are not limited to, monoethanolamine, diethanolamine, triethanolamine, N-methyldiethanolamine, diisopropylamine, diglycolamine, 2-amino-2-methyl-1-propanol, piperazine, ethoxyethanol-tert-butylamine, and any combination thereof. In more particular examples, the solvent blends may comprise at least about 3 wt. %, at least about 4 wt. %, at least about 5 wt. %, at least about 6 wt. %, at least about 7 wt. %, at least about 8 wt. %, at least about 9 wt. %, at least about 10 wt. %, at least 15 wt. %, or at least about 20 wt. % of the at least one amine solvent, as measured relative to the solvent blend as a whole. The at least one amine solvent may be present in the solvent blends in a non-zero amount, preferably in an amount less than about 25 wt. % relative to the solvent blend as a whole. Without being bound by theory or mechanism, the at least one disulfide solvent may outgas hydrogen sulfide as a result of decomposition, and the at least one amine solvent may aid in sequestering the hydrogen sulfide through an acid-base interaction. The at least one amine solvent may also promote carbon dioxide absorption through a similar mechanism. Such absorption of acid gases may provide protection against corrosion. In addition, the at least one amine solvent may increase the reaction rate between the at least one disulfide solvent and the elemental sulfur undergoing dissolution therewith, as well as improve compatibility with EPDM seals, in a non-limiting example. The at least one amine solvent may also promote sequestration of $H_2S$, which may also decrease odor and corrosiveness of the solvent blends. The at least one ketone solvent, discussed below, may aid in masking the smell of the at least one amine solvent.

In more specific examples, the co-solvents of the solvent blends may include one or more amines that comprise or consist essentially of monoethanolamine (MEA), diethanolamine (DEA), or any combination thereof, preferably in a combined amount at least about 0.1 wt. %, at least about 0.2 wt. %, at least about 0.3 wt. %, at least about 0.4 wt. %, at least about 0.5 wt. %, at least about 0.6 wt. %, at least about 0.7 wt. %, at least about 0.8 wt. %, at least about 0.9 wt. %, or at least about 1.0 wt. %, as measured relative to the co-solvents as a whole. MEA and/or DEA may increase a rate of sulfur uptake within the solvent blends by serving as a catalyst for promoting the reaction of DMDS with elemental sulfur, afford corrosion protection for metals, such as carbon steel, contacting the solvent blends, and/or improve, or increase compatibility of the solvent blends with EPDM rubber. MEA and DEA may be especially effective in these roles at lower temperatures.

In some or other more specific examples, the co-solvents of the solvent blends may include one or more amines that comprise or consist essentially of triethanolamine (TEA), optionally in further combination with MEA and/or DEA. At least about 5 wt. % TEA or at least about 10 wt. % TEA, as measured relative to the solvent blend as a whole, may be present in particular examples. In still more specific examples, the co-solvents of the solvent blends may include one or more amines that comprise or consist essentially of at least about 5 wt. % TEA, at least about 6 wt. % TEA, at least about 7 wt. % TEA, at least about 8 wt. % TEA, or at least about 9 wt. % TEA, as measured relative to the co-solvents as a whole.

In some or other more specific examples, the co-solvents of the solvent blends may include one or more amines that comprise or consist essentially of methyldiethanolamine (MDEA), optionally in further combination with MEA, DEA and/or TEA. At least about 5 wt. % MDEA or at least about 10 wt. % MDEA, as measured relative to the solvent blend as a whole, may be present in particular examples. In still more specific examples, the co-solvents of the solvent blends may include one or more amines that comprise or consist essentially of at least about 5 wt. % MDEA, at least about 6 wt. % MDEA, at least about 7 wt. % MDEA, at least about 8 wt. % MDEA, or at least about 9 wt. % MDEA, as measured relative to the co-solvents as whole.

The solvent blends may comprise up to about 25 wt. % of the at least one ketone solvent, as measured relative to the solvent blend as a whole. Suitable ketones may include, but are not limited to, acetone, methyl ethyl ketone (2-butanone), dibutyl ketone, dipropyl ketone, diisobutyl ketone, or any combination thereof. In more particular examples, the solvent blends may comprise at least about 3 wt. %, at least about 4 wt. %, at least about 5 wt. %, at least about 6 wt. %, at least about 7 wt. %, at least about 8 wt. %, at least about 9 wt. %, at least about 10 wt. %, at least 15 wt. %, or at least about 20 wt. % of the at least one ketone solvent. The at least one ketone solvent may be present in the solvent blends in a non-zero amount, preferably in an amount less than about 25 wt. % relative to the solvent blend as a whole. Without being bound by theory or mechanism, the at least one ketone solvent may improve the contact angle between the at least one disulfide solvent and the elemental sulfur to aid in promoting dissolution, increase compatibility with EPDM seals, and decrease viscosity, in non-limiting examples. In addition, the strong odor of these ketone solvents may promote masking of the odor of the at least one disulfide solvent and/or the at least one amine solvent as well.

The solvent blends may comprise up to about 50 wt. % of the at least one ester solvent, as measured relative to the solvent blend as a whole. Suitable esters may include, but are not limited to, lactic acid (lactate) esters, glycolic acid (glycolate) esters, or any combination thereof. Preferably, the at least one ester solvent may comprise or consist essentially of ethyl lactate. In more particular examples, the solvent blends may comprise at least about 15 wt. %, at least about 20 wt. %, at least about 25 wt. %, at least about 30 wt. %, at least about 35 wt. %, or at least about 40 wt. % of the at least one ester solvent. The at least one ester solvent may be present in the solvent blends in a non-zero amount, preferably in an amount less than about 50 wt. % relative to the solvent blend as a whole. Without being bound by theory or mechanism, the at least one ester solvent may increase compatibility with EPDM seals, and serve as an acid precursor to promote dissolution of an acid-soluble material under appropriate conditions. In addition, the strong (and generally pleasant) odor of ester solvents may aid in promoting masking of the odor of the at least one disulfide solvent and/or the additional co-solvents. Ethyl lactate, for example, may contribute a lemon-like scent to the solvent blends. Ethyl lactate and other ester solvents may also suppress coupling of thiols to reform disulfides, thereby contributing to odor suppression in that respect as well.

As referenced above, solids in addition to elemental sulfur that may undergo dissolution according to the disclosure herein may include inorganic sulfides and organic materials such as, for example, polyaromatic compounds (particularly asphaltenes), diamondoid compounds, paraffinic compounds, and any combination thereof. Such methods may comprise: providing a solvent blend comprising at least one disulfide solvent, at least one amine solvent, at least one ketone solvent, and at least one ester solvent; identifying one or more solids to be contacted by the solvent blend; adjusting a composition of the solvent blend to afford selectivity for dissolution of at least a portion of the one or more solids; and contacting the solvent blend with elemental sulfur and the one or more solids to promote at least partial dissolution thereof. Contacting the solids with the solvent blend may take place in continuous circulation or by "soaking" in non-limiting examples. In addition, contacting may take place under conditions wherein at least partial hydrolysis of the at least one ester solvent takes place, which may promote chelation of inorganic solids.

In some embodiments, the one or more solids contacted with the solvent blend or an at least partially spent variant thereof may comprise at least a portion of an oilfield assembly. As used herein, the term "oilfield assembly" may comprise any portion of a tool, equipment, pipeline, wellbore, tank, or the like that may be contacted with the solvent blends disclosed herein or an at least partially spent variant thereof in the course of performing an oilfield job. Oilfield jobs in which the solvent blends may be used include, for example, drilling, production, stimulation, remediation, or the like.

Solvent blends of the present disclosure may be circulated downhole or be placed under conditions that result in conversion of at least a portion of the at least one ester solvent into the corresponding carboxylic acid and the corresponding alcohol. Ethyl lactate, for instance, in the presence of water and suitable temperatures may at least partially convert (hydrolyze) to lactic acid and ethanol, wherein the lactic acid may aid in stimulating a carbonate subterranean formation by dissolving a carbonate mineral within the subterranean matrix. Dissolution of the carbonate mineral may increase downhole permeability and improve production in a non-limiting example. In addition, the lactic acid or other carboxylic acids produced through ester hydrolysis may promote dissolution of inorganic sulfides, such as iron sulfide or arsenic sulfide in non-limiting examples, as well as other inorganic solids in a similar manner.

Embodiments disclosed herein include:

A. Methods for promoting solids dissolution using a solvent blend comprising a disulfide solvent. The methods comprise: providing a solvent blend comprising at least one disulfide solvent, at least one amine solvent, at least one ketone solvent, and at least one ester solvent; identifying one or more solids in addition to elemental sulfur to be contacted by the solvent blend; adjusting a composition of the solvent blend to afford selectivity for dissolution of at least a portion of the one or more solids; and contacting the solvent blend with elemental sulfur and the one or more solids to promote at least partial dissolution thereof.

B. Methods for promoting solids dissolution using a solvent blend comprising a disulfide solvent, particularly additional solids present in combination with one or more sulfur deposits. The methods comprise: providing a solvent blend comprising at least one disulfide solvent, at least one amine solvent, at least one ketone solvent, and at least one ester solvent; exposing the solvent blend to conditions such that at least a portion of the at least one ester solvent hydrolyzes to at least one carboxylic acid, thereby affording an at least partially spent solvent blend; and contacting the at least partially spent solvent blend with an inorganic sulfide to promote dissolution of a least a portion thereof.

Each of embodiments A, and B may have one or more of the following additional elements in any combination:

Element 1: the one or more solids comprise an organic solid material selected from the group consisting of polyaromatic compounds, diamondoid compounds, paraffinic compounds, and any combination thereof.

Element 2: wherein the polyaromatic compounds comprise an organic material selected from the group consisting of dibenzothiophene, asphaltene, pyrene, chrysene, naphthalene, and any combination thereof.

Element 2A: wherein the at least one inorganic sulfide comprises a transition metal sulfide a Group 15 sulfide, a main group sulfide, or any combination thereof.

Element 2B: wherein the at least one inorganic sulfide comprises arsenic sulfide, iron sulfide, or any combination thereof.

Element 3: wherein the diamondoid compounds comprise an organic material selected from the group consisting of adamantane, diamantane, triamantane, tetramantane, pentamantane, cyclohexamantane, super-adamantane, any isomer thereof, and any combination thereof.

Element 4: wherein the paraffinic compounds comprise at least one $C_{15}$-$C_{30}$ paraffinic wax.

Element 5: wherein the one or more solids comprise at least one solid selected from the group consisting of iron sulfides, arsenic sulfides, dibenzothiophene, asphaltenes, waxes, and any combination thereof.

Element 6: wherein the at least one disulfide solvent comprises dimethyl disulfide.

Element 7: wherein the at least one amine solvent comprises at least one amine selected from the group consisting of monoethanolamine, diethanolamine, triethanolamine, N-methyldiethanolamine, diisopropylamine, diglycolamine, 2-amino-2-methyl-1-propanol, piperazine, ethoxyethanol-tert-butylamine, and any combination thereof.

Element 8: wherein the at least one ester solvent comprises a lactate ester or a glycolate ester.

Element 9: wherein the lactate ester comprises ethyl lactate.

Element 10: wherein the at least one ketone solvent comprises diisobutyl ketone, methyl ethyl ketone, acetone, or any combination thereof.

Element 11: wherein the at least one disulfide solvent comprises about 20% or more of the solvent blend by weight.

Element 12: wherein water comprises about 20% or less of the solvent blend by weight.

Element 13: wherein the one or more solids are contacted at a temperature of about 100° F. or above.

Element 14: wherein contacting comprises continuous circulation or soaking of the one or more solids with the solvent blend.

Element 15: wherein the one or more solids are located in at least a portion of an oilfield assembly.

Element 16: wherein the at least one inorganic sulfide comprises a transition metal sulfide, a Group 15 sulfide, a main group sulfide, or any combination thereof.

Exemplary combinations applicable to A may include, but are not limited to, 1 and 2; 1 and 3; 1, 3 and 4; 1 and 3-5; 1, 3 and 5; 1, 4 and 5; 1 and 3-6; 1, 3, 5 and 6; 1, 4, 5 and 6; 1 and 4; 1 and 5; 1 and 7; 1 and 3-7; 1, 3, 5 and 7; 1, 4, 5 and 7; 1 and 8; 1 and 9; 1 and 10; 1 and 11; 1 and 12; 1 and 13; 1 and 14; 1 and 15; 3 and 4; 3-5; 3 and 5; 3-6; 3-7; 3, 4 and 7; 3 and 8; 3 and 9; 3 and 10; 3 and 11; 4 and 5; 4 and 6; 4-6; 4-7; 4 and 8; 4 and 9; 4 and 10; 4 and 11; 5 and 6; 5-7; 5 and 8; 5 and 9; 5 and 10; 5 and 11; 7 and 8; 7 and 9; 7 and 10; 7 and 11; 7 and 13, 7 and 15; 8 and 9; 8 and 10; 8 and 11; 8 and 14; 8 and 15; 9 and 10; 9 and 11; 9 and 12; 9 and 13; 9 and 13; 9 and 14; 9 and 15; 10 and 11; 10 and 12; 10 and 13; 10 and 14; 10 and 15; 11 and 12; 11 and 14; 12 and 13; 12 and 14; 12 and 15; 13 and 14; 13 and 15; and 14 and 15.

Exemplary combinations applicable to B may include, but are not limited to, 2A or 2B, and 6; 2A or 2B, and 7; 2A or 2B, and 8; 2A or 2B, and 8 and 9; 2A or 2B, and 10; 2A or 2B, and 11; 2A or 2B, and 12; 2A or 2B, and 13; 2A or 2B, and 14; 2A or 2B, and 15; 6 and 7; 6 and 8, 6, 8 and 9; 6 and 10; 6 and 11; 6 and 12; 6 and 13; 6 and 14; 6 and 15; 7 and 8; 7 and 9; 7 and 10; 7 and 11; 7 and 12; 7 and 13; 7 and 14; 7 and 15; 8 and 9; 8 and 10; 8 and 11; 8 and 12; 8 and 13; 8 and 14; 8 and 15; 9 and 10; 9 and 11; 9 and 12; 9 and 13; 9 and 14; 9 and 15; 10 and 11; 10 and 12; 10 and 13; 10 and 14; 10 and 15; 11 and 12; 11 and 13; 11 and 14; 11 and 15; 12 and 13; 12 and 14; 12 and 15; 13 and 14; 13 and 15; and 14 and 15.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed, including the lower limit and upper limit. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A method comprising:
   providing a solvent blend comprising at least one disulfide solvent, at least one amine solvent, at least one ketone solvent, and at least one ester solvent;
   identifying one or more solids in addition to elemental sulfur to be contacted by the solvent blend;
   adjusting a composition of the solvent blend to afford selectivity for dissolution of at least a portion of the one or more solids; and
   contacting the solvent blend with elemental sulfur and the one or more solids to promote at least partial dissolution thereof.

2. The method of claim 1, wherein the one or more solids comprise an organic solid material selected from the group consisting of polyaromatic compounds, diamondoid compounds, paraffinic compounds, and any combination thereof.

3. The method of claim 2, wherein the polyaromatic compounds comprise an organic material selected from the group consisting of dibenzothiophene, asphaltene, pyrene, chrysene, naphthalene, and any combination thereof.

4. The method of claim 2, wherein the diamondoid compounds comprise an organic material selected from the group consisting of adamantane, diamantane, triamantane, tetramantane, pentamantane, cyclohexamantane, super-adamantane, any isomer thereof, and any combination thereof.

5. The method of claim 2, wherein the paraffinic compounds comprise at least one $C_{15}$-$C_{30}$ paraffinic wax.

6. The method of claim 1, wherein the one or more solids comprise at least one solid selected from the group consisting of iron sulfides, arsenic sulfides, dibenzothiophene, asphaltenes, waxes, and any combination thereof.

7. The method of claim 1, wherein the at least one disulfide solvent comprises dimethyl disulfide.

8. The method of claim 1, wherein the at least one amine solvent comprises at least one amine selected from the group consisting of monoethanolamine, diethanolamine, triethanolamine, N-methyldiethanolamine, diisopropylamine, diglycolamine, 2-amino-2-methyl-1-propanol, piperazine, ethoxyethanol-tert-butylamine, and any combination thereof.

9. The method of claim 1, wherein the at least one ester solvent comprises a lactate ester or a glycolate ester.

10. The method of claim 9, wherein the lactate ester comprises ethyl lactate.

11. The method of claim 1, wherein the at least one ketone solvent comprises diisobutyl ketone, methyl ethyl ketone, acetone, or any combination thereof.

12. The method of claim 1, wherein the at least one disulfide solvent comprises about 20% or more of the solvent blend by weight and wherein water comprises about 20% or less of the solvent blend by weight.

13. The method of claim 1, wherein the one or more solids are contacted at a temperature of about 100° F. or above.

14. The method of claim 1, wherein contacting comprises continuous circulation or soaking of the one or more solids with the solvent blend.

* * * * *